United States Patent [19]

Murakami et al.

[11] 4,097,487

[45] Jun. 27, 1978

[54] PYRROLIDINYL AND PIPERIDINYL BENZAMIDE DERIVATIVES

[75] Inventors: Masuo Murakami; Kozo Takahashi, both of Tokyo; Yasufumi Hirata, Ageo; Mutsuo Takashima, Kawagoe; Sumio Iwanami, Ageo; Osamu Hasegawa, Kamifukuoka; Yoshihisa Nozaki, Tokyo; Shiro Tachikawa, Omiya; Masaaki Takeda, Urawa; Shinji Usuda, Matsudo, all of Japan

[73] Assignee: Yamanouchi Pharmaceutical Co., Ltd., Tokyo, Japan

[21] Appl. No.: 671,583

[22] Filed: Mar. 29, 1976

[30] Foreign Application Priority Data

| Apr. 2, 1975 | Japan | 50-39957 |
| Dec. 17, 1975 | Japan | 50-150948 |
| Dec. 29, 1975 | Japan | 51-156396 |
| Dec. 27, 1975 | Japan | 51-157835 |
| Dec. 27, 1975 | Japan | 51-157834 |
| Dec. 29, 1975 | Japan | 51-156394 |

[51] Int. Cl.² ............... C07D 207/16; C07D 211/60
[52] U.S. Cl. .................. 260/326.85; 260/287 D; 260/293.88; 260/295 AM; 260/308 B; 260/326.1; 260/326.8; 260/326.82; 260/326.87; 260/347.2; 260/347.3; 260/558 S; 260/558 A; 260/558 D; 424/267; 424/274
[58] Field of Search ........... 260/320.1, 326.82, 326.85, 260/326.87, 293.88

[56] References Cited

U.S. PATENT DOCUMENTS

| 3,577,440 | 5/1971 | Lunsford et al. | 260/326.85 |
| 3,900,481 | 8/1975 | Banitt et al. | 260/321.85 |
| 3,975,402 | 8/1976 | Kuenzy | 260/326.82 |

*Primary Examiner*—Donald G. Daus
*Assistant Examiner*—David E. Wheeler
*Attorney, Agent, or Firm*—Burgess, Ryan and Wayne

[57] ABSTRACT

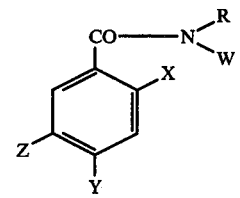

wherein R represents a hydrogen atom or a lower alkyl group; X represents a lower alkoxy group; Y represents a hydrogen atom, an amino group, or a mono- or di-lower alkylamino group; Z represents a halogen atom, a lower alkoxy group, a lower alkylthio group, a lower alkylsulfinyl group, a lower alkylsulfonyl group, a sulfamoyl group, or a lower alkylsulfamoyl group; said Y and Z may combine to form —N=N—NH—; W represents a group shown by the formula

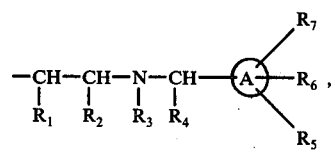

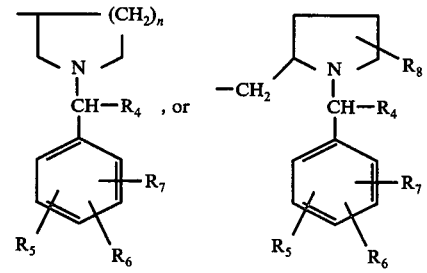

(wherein A represents a phenyl group, a cyclohexyl group, a furyl group, or a pyridyl group; $R_1$, $R_2$, and $R_4$, which may be the same or different, each represents a hydrogen atom, a lower alkyl group, or a phenyl group; $R_3$ represents a lower alkyl group, a phenyl lower alkyl group, or a di-lower alkylamino lower alkyl group; $R_5$, $R_6$, and $R_7$, which may be the same or different, each represents a hydrogen atom, a halogen atom, a lower alkoxy group, a lower alkylthio group, a lower alkylsulfinyl group, a lower alkylsulfonyl group, or a trifluoromethyl group; $R_8$ represents a lower alkyl group; and $n$ represents 1 or 2), a 1-ethyl-5-phenyl-2-pyrrolidinylmethyl group, a 1-ethyl-2-isoindolinylmethyl group, a 2-ethyl-1,2,3,4-tetrahydro-4-isoquinolyl group, a 2-(2-phenylpyrrolidino)ethyl group, a 2-(2-isoindolinyl)ethyl group, or a 2-(1,2,3,4-tetrahydro-2-isoquinolyl)ethyl group and the pharmaceutically acceptable non-toxic salts thereof.

The compounds of this invention are strong central nervous system depressants, in particular strong antipsychotics.

13 Claims, No Drawings

PYRROLIDINYL AND PIPERIDINYL BENZAMIDE DERIVATIVES

DETAILED DESCRIPTION OF THE INVENTION

The present invention relates to novel benzamide derivatives and more particularly, it relates to the benzamide derivatives represented by formula III

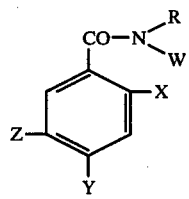

wherein R represents a hydrogen atom or a lower alkyl group; X represents a lower alkoxy group; Y represents a hydrogen atom, an amino group, or a mono- or di-lower alkylamino group; Z represents a halogen atom, a lower alkoxy group, a lower alkylthio group, a lower alkylsulfinyl group, a lower alkylsulfonyl group, a sulfamoyl group, or a lower alkylsulfamoyl group; said Y and Z may combine to form —N=N—NH—; W represents a group represented by the formula

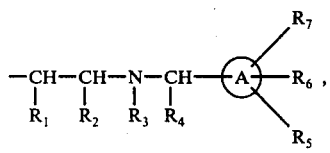

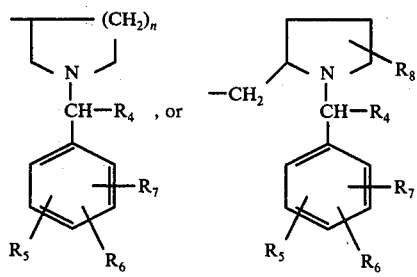

(wherein A represents a phenyl group, a cyclohexyl group, a furyl group, or a pyridyl group; $R_1$, $R_2$, and $R_4$, which may be the same or different, each represents a hydrogen atom, a lower alkyl group, or a phenyl group; $R_3$ represents a lower alkyl group, a phenyl lower alkyl group, or a di-lower alkylamino lower alkyl group; $R_5$, $R_6$, and $R_7$, which may be the same or different, each represents a hydrogen atom, a halogen atom, a lower alkoxy group, a lower alkylthio group, a lower alkylsulfinyl group, a lower alkylsulfonyl group, or a trifluoromethyl group; $R_8$ represents a lower alkyl group, and n represents 1 or 2), a 1-ethyl-5-phenyl-2-pyrrolidinylmethyl group, a 1-ethyl-2-isoindolinylmethyl group, a 2-ethyl-1,2,3,4-tetrahydro-4-isoquinolyl group, a 2-(2-phenylpyrrolidino)ethyl group, a 2-(2-isoindolinyl)ethyl group, or a 2-(1,2,3,4-tetrahydro-2-isoquinolyl)ethyl group
and the pharmaceutically acceptable nontoxic salts thereof.

The compounds of formula III of this invention are novel and possess a very strong central nervous system (CNS) depressant activity, in particular, a very strong antipsychotic activity and thus are indicated as strong CNA depressants, in particular, strong antipsychotics.

The terminology used in this specification and claims is as follows: the term "lower alkyl group" means a straight or branched chain alkyl group having 1-6 carbon atoms and includes, for example, methyl group, ethyl group, propyl group, isopropyl group, n-butyl group, isobutyl group, sec-butyl group, tert-buty group, amyl group, isoamyl group, and n-hexyl group. The term "lower alkoxy group" means a straight or branched chain alkoxy group having 1-6 carbon atoms and includes, for example, methoxy group, ethoxy group, propoxy group, isopropoxy group, n-butoxy group, amyloxy group, n-hexyloxy group, etc. Also, the term "halogen atom" includes fluorine atom, chlorine atom, bromine atom, and iodine atom.

Furthermore, when Y and Z combine to form —N+N—NH— in the compound of formula III of this invention, tautomers exist as shown by the following formula:

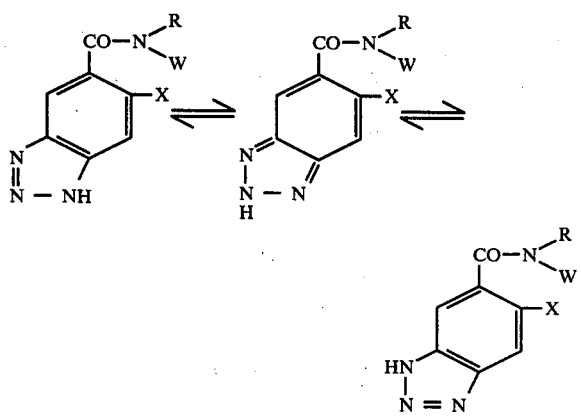

Now, one of the preferred homologs of the compound of this invention shown by formula III is the benzamide derivative shown by the formula:

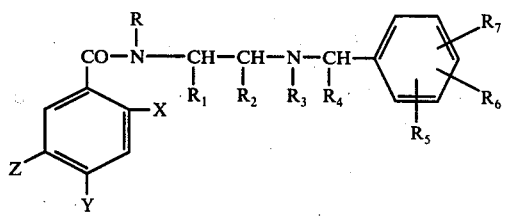

(wherein R, $R_1$, $R_2$, $R_3$, $R_4$, $R_5$, $R_6$, $R_7$, X, Y, and Z have the same meaning as defined above.)

The more preferred homolog among the aforesaid homologs is the benzamide derivative represented by the formula

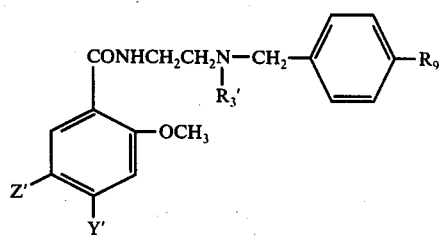

(wherein Y' represents a hydrogen atom, an amino group, or a mono- or di-lower alkylamino group; Z' represents a halogen atom an a ethyl sulfonyl group; $R_3'$ represents a lower alkyl group; and $R^9$ represents a hydrogen atom, a halogen atom, or a lower alkoxy group.) The other one of preferred homologs of the compound of this invention shown by formula III is the benzamide derivative shown by the formula

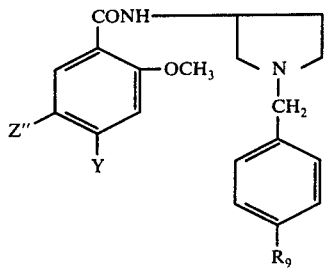

wherein $R_9$ and Y have the same meanings as defined above and Z" represents a halogen atom or an ethylsulfonyl group; said Y and Z" may combine to form —N=N—NH—.

Still other one of the preferred homologs of the compound of this invention shown by formula III is the benzamide derivative shown by the formula

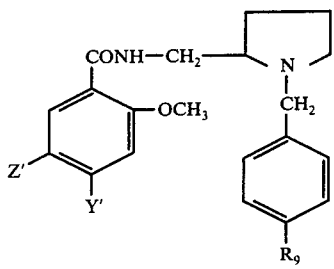

(wherein $R_9$, Y', and Z' have the same meanings as defined above.)

Practical examples of the preferred compounds of this invention are illustrated below:

N-[2-(N'-benzyl-N'-methylamino)ethyl]-4-amino-5-chloro-2-methoxybenzamide,
N-[2-(N'-ethyl-N'-p-methoxyphenylmethylamino)ethyl]-4-amino-5-chloro-2-methoxybenzamide,
N-[2-(N'-m-chlorophenylmethyl-N'-ethylamino)ethyl]-4-amino-5-chloro-2-methoxybenzamide,
(N-[2-(N'-p-chlorophenylmethyl-N'-ethylamino)ethyl]-4-amino-5-chloro-2-methoxybenzamide,
N-[2-(N'-benzyl-N'-ethylamino)ethyl]-4-amino-5-chloro-2-methoxybenzamide,
N-[2-(N'-p-chlorophenylmethyl-N'-ethylamino)ethyl]-3-ethylsulfonyl-6-methoxybenzamide,
N-[2-(N'-ethyl-N'-p-fluorophenylmethylamino)ethyl]-4-amino-5-chloro-2-methoxybenzamide,
N-(1-benzyl-3-pyrrolidinyl)-4-amino-5-chloro-2-methoxybenzamide,
N-(1-p-chlorophenylmethyl-3-pyrrolidinyl)-4-amino-5-chloro-2-methoxybenzamide,
N-(1-benzyl-5-methyl-2-pyrrolidinylmethyl)-4-amino-5-chloro-2-methoxybenzamide;
N-(1-benzyl-5-methyl-2-pyrrolidinylmethyl)-5-ethylsulfonyl-2-methoxybenzamide,
N-[2-(N'-p-chlorophenylmethyl-N'-ethylamino)ethyl]-5-chloro-4-ethylamino-2-methoxybenzamide,
N-[2-(N'-p-chlorophenylmethyl-N'-ethylamino)ethyl]-5-chloro-4-dimethylamino-2-methoxybenzamide,
N-(1-p-chlorophenylmethyl-3-pyrrolidinyl)-5-chloro-4-ethylamino-2-methoxybenzamide, and
N-(1-p-chlorophenylmethyl-3-pyrrolidinyl)-5-chloro-4-dimethylamino-2-methoxybenzamide.

The pharmaceutically acceptable nontoxic salts of the compounds of this invention shown by formula III include the acid-addition salts thereof with an inorganic acid such as hydrochloric acid, hydrobromic acid, sulfuric acid, nitric acid, phosphoric acid or an organic acid such as citric acid, acetic acid, lactic acid, tartaric acid, succinic acid, fumaric acid, maleic acid, etc., and the quaternary ammonium salts obtained by the reaction thereof and methyl iodide, ethyl iodide, methyl bromide, benzyl bromide, dimethylsulfuric acid, methyl p-toluenesulfonate, methanesulfonic acid, etc.

Hitherto, various compounds are known as the compounds possessing CNS depressant activity, in particular, antipsychotic activity and among these compounds, chlorpromazine is well-known and commercially available. However, the activity of chlorpromazine is yet insufficient and hence the discovery of medicaments possessing more excellent antipsychotic activity has been desired.

Since the compounds of this invention shown by formula III possess strong activities of reducing the conditioned avoidance response, the apomorphine-induced stereotyped behavior, and the methamphetamine-induced stereotyped behavior, they show a very strong CNS depressant activity, in particular, antipsychotic activity. Furthermore, since the compounds of this invention are less cataleptogenic activity, the representation of extrapyramidal syndrome which is the main side reaction of antipsychotics is rare and thus the compounds show selective activities. That is, the compounds of this invention shown by formula III are very strong CNS depressants, in particular, antipsychotics having high selectivity. Still further, the compounds of this invention shown by formula III also have a strong vasodilating action.

Now, Dutch Pat. No. 7,304,557 discloses that the N-(1-substituted-3-pyrrolidinyl)benzamide and thiobenzamide shown by the general formula

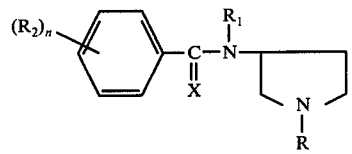

(wherein R represents a cycloalkyl group, a phenyl group, or a phenyl lower alkyl group; $R_1$ represents a hydrogen atom, a lower alkyl group having 1–8 carbon atoms, or a phenyl group; $R_2$ represents a halogen atom, a lower alkyl group, a lower alkoxy group, an amino group, a nitro group, a monoalkylamino group, a dialkylamino group, a mercaptomethyl group, an acetamide group, a sulfamoyl group, a cyano group, a hydroxy group, a benzyloxy group, or a trifluoromethyl group; X represents an oxygen atom or a sulfur atom; and n represents an integer of 0–3) have a strong antiemetic activity.

In the Dutch patent, when R of the above general formula is a phenyl lower alkyl group, the compounds of the formula may partially overlap, from a theoretical view point, the compounds of this invention shown by formula III wherein W is a group shown by

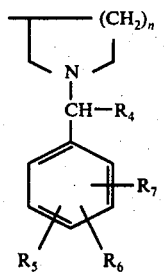

However, among the compounds of the general formula in the Dutch patent, wherein R is a phenyl lower alkyl group, the practical examples disclosed in the patent are only N-(1-benzyl-3-pyrrolidinyl)-3,4,5-trimethoxybenzamide, N-(1-benzyl-3-pyrrolidinyl)-N-phenyl-4-chlorobenzamide, N-(1-benzyl-3-pyrrolidinyl)-N-phenylbenzamide, and N-(1-benzyl-3-pyrrolidinyl)benzamide, which correspond to the compounds of the formula wherein R is a benzyl group and are not disclosed in the compounds of this invention shown by formula III, and further there are no practical descriptions about the pharmacological data of these compounds in the specification of the Dutch patent.

That is, the compounds of this invention shown by formula III are novel compounds which are not disclosed in the Dutch patent and possess a remarkably strong antipsychotic activity as compared with that of N-(1-cyclohexyl-3-pyrrolidinyl)-4-amino-5-chloro-2-methoxybenzamide, which is said to have the strongest antiemetic activity according to the Dutch patent, and the above-described benzamide compounds which are practically disclosed examples.

Also, as a compound having a similar chemical structure to those of the compounds of this invention shown by formula III, metoclopramide shown by the formula

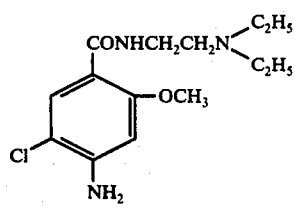

is well-known and is commercially available as antiemetics.

Furthermore, sulpiride shown by the formula

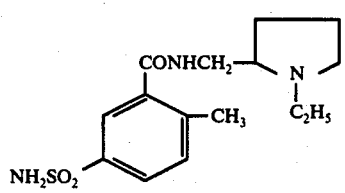

(Japanese Pat. Publication No. 23,496/'69), sultopiride shown by the formula

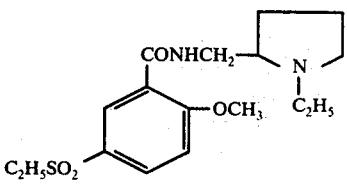

(Japanese Pat. Publication No. 23,496/'69), and N-[2-(N'-benzyl-N'-methylamino)ethyl]-3,4,5-trimethoxybenzamide shown by the formula

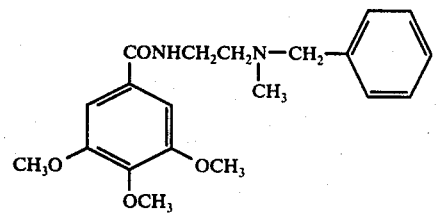

(Chemical Abstracts, 53, p 11417e(1959)) are known, However, the compounds of this invention shown by formula III have remarkably stronger antipsychotic activity as compared with these known compounds.

The compound of this invention shown by formula III can be prepared by reacting benzoic acid shown by the formula I

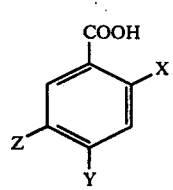

(wherein X, Y, and Z have the same meanings as in formula III) or the reactive derivative thereof and the amine shown by the formula II

(wherein R and W have the same meanings as in formula III.)

As the reactive derivatives of benzoic acid shown by formula I, there are illustrated an acid halide such as acid chloride, acid bromide, etc.; an acid azide; an ester such as methyl ester, ethyl ester, p-nitrophenyl ester, p-chlorophenyl ester, etc., a symmetric acid anhydride; a mixed acid anhydride such as an alkyl carbonate mixed acid anhydride prepared by reacting the benzoic acid (I) and an alkyl halocarbonate (e.g., methyl chlorocarbonate, ethyl chlorocarbonate, and ethyl bromocarbonate ) and a mixed acid anhydride prepared by reacting the benzoic acid (I) and an acid (e.g., alkylphosphoric acid, alkylphosphorous acid, and sulfuric acid) or the reactive derivatives thereof; and an active amide such as acid imidazolide or acid pyrrolidide prepared by reacting benzoic acid (I) and N,N'-carbonyldiimidazole, N,N'-thionyldiimidazole, or N,N'-carbonyldipyrrole and an acid 2,4-dimethylpyrazolide prepared by reacting the acid hydrazide of the benzoic acid (I) and acetylacetone.

The reaction of producing the compound of this invention is practically carried out by condensing the benzoic acid shown by formula I or the reactive derivative thereof and an equimolar or excessive molar amount of the amine shown by formula II.

When the benzoic acid shown by formula I is a free carboxylic acid, the benzoic acid (I) may be reacted with the amine of formula II at room temperature or under heating in an inert solvent in the presence of a condensing agent such as N,N'-dicyclohexylcarbodiimide, titanium tetrachloride, or a phosphorus halide (e.g., phosphorus trichloride, phosphorus oxychloride, diethyl chlorophosphite, o-phenylene chlorophosphite, and ethyl dichlorophosphite). Furthermore, the compound of this invention may be also produced by reacting preliminary the amine of formula II with the phosphorus halide in an inert solvent and then reacting the product thus obtained with benzoic acid (I). For example, in the case of using the amine of formula II wherein R is hydrogen atom and the phosphorus halide is phosphorus trichloride the amine (II) is first reacted with about ½ mole of phosphorus trichloride in an inert solvent under cooling or at room temperature in the presence of a tertiary base such as triethylamine, pyridine, N,N-dimethylaniline, etc., and then reacting the product thus obtained with the benzoic acid (I) in an inert solvent at room temperature or under heating, preferably under refluxing.

When an acid halide is used as the reactive derivative of the benzoic acid (I), the reaction is usually carried out in water under cooling or at room temperature in the presence of an alkali such as sodium hydroxide, potassium hydroxide, etc., or, in an inert solvent under cooling or at room temperature in the presence of a tertiary base such as triethylamine, pyridine, N,N-dimethylaniline, etc. When an acid azide is used as the reactive derivative of the benzoic acid (I), the reaction is usually carried out in water under cooling or at room temperature in the presence of an alkali such as sodium hydroxide, potassium hydroxide, etc. When an ester is used as the reactive derivative of the benzoic acid (I), the reaction is usually carried out in an inert solvent at room temperature or under heating, preferably under refluxing. When a symmetric acid anhydride or a mixed acid anhydride such as the alkyl carbonate mixed acid anhydride is used as the reactive derivative of the benzoic acid (I), the reaction is usually carried out in an inert solvent at room temperature or under heating in the presence of, if necessary, a tertiary base such as triethylamine, pyridine, N,N-dimethylaniline, etc. Also, when an active amide is used as the reactive derivative of the benzoic acid (I), the reaction is usually carried out in an inert solvent at room temperature or under heating. In addition, in these reactions, the reactive derivative of the benzoic acid (I) may be reacted, if desired, with the amine of formula II without being isolated from the reaction mixture thereof.

The inert solvent used in the reaction of this invention is an inert organic solvent which does not participate to the reaction and preferred examples of the organic solvent are benzene, toluene, xylene, methanol, ethanol, isopropanol, ether, dioxane, tetrahydrofuran, chloroform, dichloromethane, dichloroethane, etc. They may be properly selected according to the nature of the reactive derivative used.

In addition, the compound of this invention shown by formula III which $R_5$, $R_6$, and/or $R_7$ is a lower alkylthio group can be converted into the compound of this invention shown by formula III in which $R_5$, $R_6$, and/or $R_7$ is a lower alkylsulfinyl group or a lower alkylsulfonyl group by oxidizing. Practically, the aforesaid conversion can be performed by oxidizing the compound under suitable condition which does not give influences on the other portions of the compound of formula III in which $R_5$, $R_6$, and/or $R_7$ is a lower alkylthio group. In this case, ordinary oxidizing agent such as hydrogen peroxide, potassium permanganate, potassium metaperiodate, etc., can be used.

Also, the compound of this invention shown by formula III in which Y and Z combine to form —N=•N—NH can be obtained by reacting the amine (II) with the acid halide of the benzoic acid (I) in which Y and Z combine to form —N=N—NH— whose the —NH— group is protected by such as an acetyl group, etc., and then releasing the protecting group by a conventional manner such as hydrolysis, etc.

The compound of this invention shown by formula III thus prepared can be isolated and purified by an ordinary chemical operation such as extraction, recrystallization, column chromatography, etc.

In following Experiment I, the compounds of this invention were compared with chloropromazine which is typical antipsychotics and other known structural similar compounds by experiment about the activity of reducing the apomorphine-induced stereotyped behavior.

Experiment I

According to the method of Janssen et al (Arzneim. Forsch., 15, 104(1965)), each of rats (male, Wistar, 200–250 g.) was placed in each observation cage, a test sample was administered subcutaneously to the rat, and after 30 minutes, 1.25 mg/Kg of apomorphine was also administered intravenously to the rat. After 5 minutes, 10 minutes, and 20 minutes since then, the symptom of the apomorphine-induced stereotyped behavior was observed in each case. Then, from the relation of the ratio of inhibition and the amount of the test sample used, $ED_{50}$ was determined, the results — are shown in Table I.

Table 1

| Test sample | $ED_{50}$* (mg./kg.) |
|---|---|
| Known compound: | |
| Chlorpromazine | 2.5 |
| Metoclopramide | 4.1 |
| Sulpiride | >100 |
| Sultopiride | 18 |
| N-(1-cyclohexyl-3-pyrrolidinyl)-4-amino-5-chloro-2-methoxybenzamide | 1.8 |
| N-(1-benzyl-3-pyrrolidinyl)-3,4,5-trimethoxybenzamide | >10 |
| N-[2-(N'-benzyl-N'-methylamino)ethyl]-3,4,5-trimethoxybenzamide | >30 |
| Compound of this invention: | |
| N-[2-(N'-benzyl-N'-methylamino)ethyl]-4-amino-5-chloro-2-methoxybenzamide | 0.54 |
| N-[2-(N'-ethyl-N'-p-methoxyphenylmethylamino)ethyl]-4-amino-5-chloro-2-methoxybenzamide | 0.3 |
| N-[2-(N'-m-chlorophenylmethyl-N'-ethylamino)-ethyl]-4-amino-5-chloro-2-methoxybenzamide | 0.3 |
| N-[2-(N'-p-chlorophenylmethyl-N'-ethylamino)ethyl]-4-amino-5-chloro-2-methoxybenzamide | 0.18 |
| N-[2-(N'-benzyl-N'-ethylamino)ethyl]-4-amino-5-chloro-2-methoxybenzamide | 0.2 |
| N-[2-(N'-p-chlorophenylmethyl-N'-ethylamino)ethyl]-3-ethylsulfonyl-6-methoxybenzamide | 0.47 |
| N-[2-(N'-ethyl-N'-p-fluorophenylmethylamino)ethyl]-4-amino-5-chloro-2-methoxybenzamide | 0.18 |
| N-(1-benzyl-3-pyrrolidinyl)-4-amino-5-chloro-2-methoxybenzamide | 0.22 |
| N-(1-p-chlorophenylmethyl-3-pyrrolidinyl)-4-amino-5-chloro-2-methoxybenzamide | 0.18 |
| N-(1-benzyl-5-methyl-2-pyrrolidinylmethyl)-4- | |

Table 1-continued

| Test sample | $ED_{50}$* (mg./kg.) |
|---|---|
| N-(1-benzyl-5-methyl-2-pyrrolidinylmethyl)-5-amino-5-chloro-2-methoxybenzamide | 0.18 |
| N-(1-benzyl-5-methyl-2-pyrrolidinylmethyl)-5-ethylsulfonyl-2-methoxybenzamide | 0.3 |

*The activity of reducing apomorphine-induced stereotyped behavior.

As clear from the results shown in the above table, the compounds of this invention shown by formula III have a remarkably strong activity of reducing the apomorphine-induced stereotyped behavior as compared with chlorpromazine which is typical antipsychotics and other known structural similar compounds, and thus it is clear that the compounds of this invention had stronger CNS depressant activity, in particular antipsychotic activity than these known compounds.

In following Experiment II, the compounds of this invention were compared with chlorpromazine which is a typical antipsychotic by experiment about the activity of reducing the conditioned avoidance response and the methamphetamin-induced stereotyped behavior.

Experiment II (a) Activity of reducing the conditioned avoidance response:

By a shuttle box method using rats (male, Wister, about 300 g.), a test sample was administered subcutaneously to the rats, after 30 minutes, a conditioned stimulation (buzzer noise for at longest 5 seconds) was applied, and then the avoidance response was observed. Then, from the relation of the ratio of inhibition of avoidance response and the amount of the test sample used, $ED_{50}$ was determined. In addition, the training of applying an electric stimulation (A.C. 40 volts) as an unconditioned stimulation from a grid on a floor for at longest 5 seconds was applied to rats at 20 times/day for 6 days and the rats showing the ratio of avoidance response of higher than 80% were used in the experiment.

(b). Activity of reducing the methamphetamin-induced stereotyped behavior:

By referring to the aforesaid method of Janssen et al and the method of Weisman et al (J. Pharmacol. Exp. Ther., 151, 339(1966)), each of rats (male, Wister, 8 weeks age) was placed in each observation cage. A test sample was administered subcutaneously to the rats, after 30 minutes, 5 mg./kg. of methamphetamine was administered intraperitoneally, and then after 60 minutes and 90 minutes since then, the symptom of the methamphetamin-induced stereotyped behavior was observed. From the relation of the ratio of inhibition and the amount of the test sample used, $ED_{50}$ was determined.

The results are shown in Table II.

Table II

| Test sample | a) $ED_{50}$ (mg/kg) | b) $ED_{50}$ (mg/kg) |
|---|---|---|
| Chlorpromazine | 0.8 | 3.0 |
| N-[2-(N'-benzyl-N'-methylamino)ethyl]-4-amino-5-chloro-2-methoxybenzamide | 0.2 | 3.0 |
| N-[2-(N'-m-chlorophenylmethyl-N'-ethylamino)ethyl]-4-amino-5-chloro-2-methoxybenzamide | — | 1.0 |
| N-[2-(N'-p-chlorophenylmethyl-N'-ethylamino)ethyl]-4-amino-5-chloro-2-methoxybenzamide | 0.1 | 1.0 |
| N-[2-(N'-benzyl-N'-ethylamino)ethyl]-4-amino-5-chloro-2-methoxybenzamide | 0.1 | 1.8 |
| N-[2-(N'-p-chlorophenylmethyl-N'-ethylamino)ethyl]-3-ethylsulfonyl-6-methoxybenzamide | — | 3.0 |
| N-(1-benzyl-3-pyrrolidinyl)-4-amino-5-chloro-2-methoxybenzamide | 0.3 | 0.72 |
| N-(1-p-chlorophenylmethyl-3-pyrrolidinyl)-4-amino-5-chloro-2-methoxybenzamide | 0.1 | — |
| N-(1-benzyl-5-methyl-2-pyrrolidinyl)-4-amino-5-chloro-2-methoxybenzamide | 0.18 | 1.0 |
| N-(1-benzyl-5-methyl-2-pyrrolidinylmethyl)-5-ethylsulfonyl-2-methoxybenzamide | 0.3 | 1.8 |

As clear from the results shown in the above table, the compounds of this invention possess a strong activity of reducing the conditioned avoidance response and the methamphetamine-induced stereotyped behavior and thus it is clear that the compounds of this invention have a strong CNS depressant activity, in particular antipsychotic activity.

In following Experiment III, the compounds of this invention shown by formula III were compared with chlorpromazine by experiment about the cataleptogenic activity and acute toxicity.

Experiment III (a) Cataleptogenic activity:

By referring to the method by Curvoisier et al (Psychotropic drugs, 373(1957)), a test sample was subcutaneously administered to mice (male, ICR, 8 weeks age) and after 30 minutes since then, the both fore-limb was forcibly hung on a horizontal metallic rod of 2 mm. diameter placed at a height of 6 cm. and when the mouse was kept in that state for 30 second, the activity of the mouse was considered to be a positive cataleptogenic activity. From the relation of the ratio of inhibition and the amount of the test sample used, $ED_{50}$ was determined.

(b) Acute toxicity:

A test sample was administered to mice (male, ICR, 8 week age) by an intravenous injection and then $LD_{50}$ was determined by an up-down method.

The both results are shown in Table III.

Table III

| Test sample | a) $ED_{50}$ (mg/kg) | b) $LD_{50}$ (mg/kg) |
|---|---|---|
| Chlorpromazine | 10 | 59 |
| N-[2-(N'-benzyl-N'-methylamino)ethyl]-4-amino-5-chloro-2-methoxybenzamide | 60 | 48 |
| N-(1-benzyl-5-methyl-2-pyrrolidinylmethyl)-4-amino-5-chloro-2-methoxybenzamide | 30 | 49 |

As clear from the results shown in the above table, the compounds of this invention is less cataleptogenic activity and thus the re-presentation of extrapyramidal syndroms which is the main side reaction of antipsychotics is considered to be less. Thus, it is clear that the compounds of this invention possess a CNS depressant activity having very high selectivity, in particular antipsychotic activity having very high selectivity.

The compounds of this invention shown by formula III can be administered orally as a form of tablets, capsules, powders, sirups, etc., or can be administered parenterally by intramuscular injection, subcutaneous injection, intravenous injection, or as a suppository, etc. The clinical dose of the compound is 10–200 mg./day for adult in the case of oral administration and 1–150 mg./day for adult in the case of parenteral administration. The dosage may be properly changed according to the condition and age of a patient.

Now, general methods of producing the compounds of this invention are illustrated below.

General method A

In 10–30 ml. of dichloromethane is suspended 0.005 mole of the benzoic acid shown by aforesaid general formula I and then 0.005–0.006 mole of triethylamine is added to the suspension to form a solution. The solution is cooled to a temperature of from −10° to −40° C. and after adding thereto 0.005–0.006 mole of ethyl chlorocarbonate, the mixture is stirred for 0.5–2 hours. Then, 0.005–0.006 mole of the amine of formula II is added to the mixture at the same temperature followed by stirring for further 2–3 hours at room temperature. After the reaction is over, the reaction mixture is cooled and after adding thereto 20 ml. of 0.5 normal hydrochloric acid, the mixture is shaked well. Then, an aqueous layer is separated from an organic layer. The organic layer is further extracted twice each with 10 ml. of water and the aqueous extract is combined with the aqueous layer recovered above. The aqueous solution thus recovered is washed with 10 ml. of dichloromethane, alkalified with a 1 normal aqueous solution of sodium hydroxide, and then extracted thrice each with 10 ml. of dichloromethane. The extract was washed with water, dried, and then the solvent is distilled off under a reduced pressure. By purifying the residue thus formed by recrystallization or column chromatography, the aimed benzamide derivative of formula III or a salt thereof is obtained.

General method B

In 10–30 ml. of dichloromethane is suspended 0.005 mole of benzoic acid shown by formula I and 0.005–0.006 mole of triethylamine is added to the suspension to form a solution. The solution is cooled to a temperature of from −10° to −40° C. and after adding thereto 0.005–0.006 mole of ethyl chlorocarbonate, the mixture is stirred for 0.5–2 hours. Then, 0.005–0.006 mole of the amine of formula II is added to the mixture at the same temperature as above followed by stirring for 0.5 hour and then the mixture is stirred for 2–3 hours at room temperature. After the reaction is over, the reaction mixture is washed with a 1 normal aqueous solution of sodium hydroxide and water and after drying, the solvent is distilled off under a reduced pressure. By purifying the residue formed by recrystallization or column chromatography, the aimed benzamide derivative of formula III or a salt thereof is obtained.

General method C

In 10–30 ml. of dichloromethane is suspended 0.005 mole of the benzoic acid shown by formula I and then 0.005–0.006 mole of triethylamine is added to the suspension to form a solution. The solution is cooled to a temperature of from −10° C. to −40° C. and after adding thereto 0.005–0.006 mole of ethyl chlorocarbonate, the mixture is stirred for 0.5–2 hour. Thereafter, 0.005–0.006 mole of the amine of formula II is added to the mixture at the same temperature as above followed by stirring for 0.5 hour, the mixture is further stirred for 2–3 hours at room temperature. After the reaction is over, the reaction mixture is washed with a 1 normal aqueous solution of sodium hydroxide and then with water and 20 ml. of 0.5 normal hydrochloric acid is added to the mixture followed by shaking well. Then, an aqueous layer formed is removed and an organic layer thus recovered is washed with water, dried, and the solvent is distilled off under a reduced pressure. By recrystallizing the crystals thus formed, the aimed benzamide derivative hydrochloride of formula III is obtained.

General method D

In a mixture of 10 ml. of hexamethylphospholamide and 10 ml. of dichloromethane is dissolved 0.004 mole of the benzoic acid or shown by formula I and then 0.0045 mole of triethylamine is added to the solution. The mixture is cooled to a temperature of from −20° to −40° C. and after adding thereto 0.004 mole of ethyl chlorocarbonate followed by stirring for 0.5 hour, 0.004 mole of the amine of formula II is added to the mixture at the same temperature as above. Then, the mixture was further stirred for 0.5 hour at the same temperature and for 2 hours at room temperature. After the reaction is over, the reaction mixture is acidified with diluted hydrochloric acid, etc., and is extracted twice each with 50 ml. of water. The extract is adjusted to pH 7 with a 1 normal aqueous solution of sodium hydroxide and by recrystallizing the crystals thus formed, the aimed benzamide derivative of formula III or a salt thereof is obtained.

EXAMPLE 1

By following general method A described above using 1.01 g. of 4-amino-5-chloro-2-methoxybenzoic acid and 1.15 g. of N-(m-methoxyphenylmethyl)-N-ethylethylenediamine, 1.51 g. of N-[2-(N'-m-methoxyphenylmethyl-N'-ethylamino)ethyl]-4-amino-5-chloro-2-methoxybenzamide was obtained.

Melting point: 109°–110° C. (recrystallized from ethyl acetate).

Elemental analysis for $C_{20}H_{26}N_3O_3Cl$:

|  | C% | H% | N% |
|---|---|---|---|
| Calculated: | 61.30 | 6.69 | 10.72 |
| Found: | 60.59 | 6.75 | 10.65 |

EXAMPLE 2

By following general method A using 1.01 g. of 4-amino-5-chloro-2-methoxybenzoic acid and 1.15 g. of N-(p-methoxyphenylmethyl)-N-ethylethylenediamine, 1.65 g. of N-[2-(N'-p-methoxyphenylmethyl-N'-ethylamino)ethyl]-4-amino-5-chloro-2-methoxybenzamide was obtained.

Melting point: 117°–119° C. (recrystallized from ethyl acetate).

Elemental analysis for $C_{20}H_{26}N_3O_3Cl$:

| | C% | H% | N% |
|---|---|---|---|
| Calculated: | 61.30 | 6.69 | 10.72 |
| Found: | 61.22 | 6.77 | 10.61 |

EXAMPLE 3

By following general method A using 1.01 g. of 4-amino-5-chloro-2-methoxybenzoic acid and 1.17 g. of N-(o-chlorophenylmethyl)-N-ethylethylenediamine, 1.51 g. of N-[2-(N'-o-chlorophenylmethyl-N'-ethylamino)ethyl]-4-amino-5-chloro-2-methoxybenzamide was obtained.

Melting point: 110°–111° C. (recrystallized from toluene).

Elemental analysis for $C_{19}H_{23}N_3O_2Cl_2$:

| | C% | H% | N% |
|---|---|---|---|
| Calculated: | 57.58 | 5.85 | 10.60 |
| Found: | 57.93 | 5.82 | 10.71 |

EXAMPLE 4

By following general method A using 1.01 g. of 4-amino-5-chloro-2-methoxybenzoic acid and 1.17 g. of N-(m-chlorophenylmethyl)-N-ethylethylenediamine, 1.47 g. of N-[2-(N'-m-chlorophenylmethyl-N'-ethylamino)ethyl]-4-amino-5-chloro-2-methoxybenzamide was obtained.

Melting point: 128°–130° C. (recrystallized from toluene).

Elemental analysis for $C_{19}H_{23}N_3O_2Cl_2$:

| | C% | H% | N% |
|---|---|---|---|
| Calculated: | 57.58 | 5.85 | 10.60 |
| Found: | 57.36 | 5.82 | 10.52 |

EXAMPLE 5

By following general method A using 1.01 g. of 4-amino-5-chloro-2-methoxybenzoic acid and 1.17 g. of N-(p-chlorophenylmethyl)-N-ethylethylenediamine, 1.51 g. of N-[2-(N'-p-chlorophenylmethyl-N'-ethylamino)ethyl]-4-amino-5-chloro-2-methoxybenzamide was obtained.

Melting point: 127°–128° C. (recrystallized from toluene).

Elemental analysis for $C_{19}H_{23}N_3O_2Cl_2$:

| | C% | H% | N% |
|---|---|---|---|
| Calculated: | 57.58 | 5.85 | 10.60 |
| Found: | 57.74 | 6.05 | 10.34 |

EXAMPLE 6

By following general method A using 1.01 g. of 4-amino-5-chloro-2-methoxybenzoic acid and 1.13 g. of N-benzyl-N-tert-butylethylenediamine, 1.40 g. of N-[2-(N'-benzyl-N'-tert-butylamino)ethyl]-4-amino-5-chloro-2-methoxybenzamide was obtained.

Melting point: 134°–135° C. (recrystallized from isopropanol).

Elemental analysis for $C_{21}H_{28}N_3O_2Cl$:

| | C% | H% | N% |
|---|---|---|---|
| Calculated: | 64.69 | 7.24 | 10.78 |
| Found: | 63.99 | 7.27 | 10.43 |

EXAMPLE 7

By following general method A using 1.01 g. of 4-amino-5-chloro-2-methoxybenzoic acid and 0.97 g. of N-(1-phenylethyl)-N-methylethylenediamine, 1.30 g. of N-[2-{N'-(1-phenylethyl)-N'-methylamino}ethyl]-4-amino-5-chloro-2-methoxybenzamide was obtained.

Melting point: 139°–140° C. (recrystallized from ethyl acetate).

Elemental analysis for $C_{19}H_{24}N_3O_2Cl$:

| | C% | H% | N% |
|---|---|---|---|
| Calculated: | 63.06 | 6.68 | 11.61 |
| Found: | 63.71 | 6.93 | 11.77 |

EXAMPLE 8

By following general method A using 1.2 g. of 3-ethylsulfonyl-6-methoxybenzoic acid and 1.0 g. of N-p-chlorophenylmethyl-N-($\beta$-diethylaminoethyl)ethylenediamine, 1.25 g. of N-[2-(N'-p-chlorophenylmethyl-N'-$\beta$-diethylaminoethylamino)ethyl]-3-ethylsulfonyl-6-methoxybenzamide hydrochloride was obtained.

Melting point: 142°–144° C.

Nuclear magnetic resonance spectra (D$_2$O):
$\delta$(p.p.m.): 1.9–2.4 (9H), 3.0–3.8 (14H), 3.85 (3H), 4.28 (2H), 6.8–8.1 (7

EXAMPLE 9

By following general method A using 1.0 g. of 4-amino-5-chloro-2-methoxybenzoic acid and 0.8 g. of N-cyclohexylmethyl-N-methylethylenediaimine, 0.5 g. of N-[2-(N'-cyclohexylmethyl-N'-methylamino)ethyl]-4-amino-5-chloro-2-methoxybenzamide was obtained.

Melting point: 115°–118° C. (recrystallized from benzene).

Elemental analysis for $C_{18}H_{28}N_3O_2Cl$:

| | C% | H% | N% |
|---|---|---|---|
| Calculated: | 61.09 | 7.97 | 11.87 |
| Found: | 60.68 | 8.34 | 11.75 |

EXAMPLE 10

By following general method B using 1.07 g. of 6-methoxy-3-methylsulfinylbenzoic acid and 0.82 g. of N-benzyl-N-methylethylenediamine, 1.3 g. of N-[2-(N'-benzyl-N'-methylamino)ethyl]-6-methoxy-3-methylsulfinylbenzamide was obtained.

Melting point: 109°–110° C. (recrystallized from isopropanol).

Elemental analysis for $C_{19}H_{24}N_2O_3S$:

| | C% | H% | N% |
|---|---|---|---|
| Calculated: | 63.31 | 6.71 | 7.77 |
| Found: | 62.82 | 6.72 | 7.50 |

EXAMPLE 11

By following general method B using 1.01 g. of 4-amino-5-chloro-2-methoxybenzoic acid and 1.15 g. of N-(o-methoxyphenylmethyl)-N-ethylethylenediamine, 1.55 g. of N-[2-(N'-o-methoxyphenylmethyl-N'-ethylamino)ethyl]-4-amino-5-chloro-2-methoxybenzamide was obtained.

Melting point: 119°–120° C. (recrystallized from toluene).

Elemental analysis for $C_{20}H_{26}N_3O_3Cl$:

|  | C% | H% | N% |
|---|---|---|---|
| Calculated: | 61.30 | 6.69 | 10.72 |
| Found: | 61.33 | 6.77 | 10.77 |

EXAMPLE 12

By following general method B using 1.15 g. of 6-methoxy-3-methylsulfonylbenzoic acid and 0.82 g. of N-benzyl-N-methylethylenediamine, 1.1 g. of N-[2-(N'-benzyl-N'-methylamino)ethyl]-6-methoxy-3-methylsulfonylbenzamide was obtained.

Melting point: 129°–130° C. (recrystallized from a mixture of isopropanol and methanol).

Elemental analysis for $C_{19}H_{24}N_2O_4S$:

|  | C% | H% | N% |
|---|---|---|---|
| Calculated: | 60.62 | 6.43 | 7.44 |
| Found: | 60.81 | 6.39 | 7.12 |

EXAMPLE 13

By following general method B using 1.0 g. of 4-amino-5-chloro-2-methoxybenzoic acid and 0.9 g. of N-benzyl-N-ethylethylenediamine, 1.3 g. of N-[2-(N'-benzyl-N'-ethylamino)ethyl]-4-amino-5-chloro-2-methoxybenzamide was obtained.

Melting point: 96°–98° C. (recrystallized from a mixture of toluene and n-hexane).

Elemental analysis for $C_{19}H_{24}N_3O_2Cl$:

|  | C% | H% | N% | Cl% |
|---|---|---|---|---|
| Calculated: | 63.06 | 6.68 | 11.61 | 9.80 |
| Found: | 63.12 | 6.76 | 11.37 | 10.09 |

EXAMPLE 14

By following general method B using 1.0 g. of 4-amino-5-chloro-2-methoxybenzoic acid and 0.9 g. of N-(o-methylphenylmethyl)-N-methylethylenediamine, 1.3 g. of N-[2-(N'-o-methylphenylmethyl-N'-methylamino)ethyl]-4-amino-5-chloro-2-methoxybenzamide was obtained.

Melting point: 118°–120° C. (recrystallized from a mixture of toluene and n-haxane (volume ratio 2:1))

Elemental analysis for $C_{19}H_{24}N_3O_2Cl$:

|  | C% | H% | N% | Cl% |
|---|---|---|---|---|
| Calculated: | 63.06 | 6.68 | 11.61 | 9.80 |
| Found: | 63.17 | 6.65 | 11.53 | 10.07 |

EXAMPLE 15

By following general method B using 1.0 g. of 4-amino-5-chloro-2-methoxybenzoic acid and 1.2 g. of N,N-dibenzylethylenediamine, 1.5 g. of N-[2-(N',N'-dibenzylamino)ethyl]-4-amino-5-chloro-2-methoxybenzamide was obtained.

Melting point: 133° C. (recrystallized from toluene).

Elemental analysis for $C_{27}H_{26}N_3O_2Cl$:

|  | C% | H% | N% | Cl% |
|---|---|---|---|---|
| Calculated: | 68.00 | 6.18 | 9.91 | 8.36 |
| Found: | 67.71 | 6.17 | 9.72 | 8.16 |

EXAMPLE 16

By following general method B using 1.0 g. of 4-amino-5-chloro-2-methoxybenzoic acid and 1.2 g. of N-o-trifluoromethylphenylmethyl-N-methylethylenediamine, 1.2 g. of N-[2-(N'-o-trifluoromethylphenylmethyl-N'-methylamino)ethyl]-4-amino-5-chloro-2-methoxybenzamide was obtained.

Melting point: 147°–149° C. (recrystallized from toluene).

Elemental analysis for $C_{19}H_{21}N_3O_2ClF_3$:

|  | C% | H% | N% | Cl% |
|---|---|---|---|---|
| Calculated: | 54.88 | 5.09 | 10.10 | 8.53 |
| Found: | 54.75 | 5.19 | 9.76 | 8.52 |

EXAMPLE 17

By following general method B using 1.0 g. of 4-amino-5-chloro-2-methoxybenzoic acid and 1.14 g. of N-(p-chlorophenylmethyl)-N-n-propylethylenediamine, 1.3 g. of N-[2-(N'-p-chlorophenylmethyl-N'-n-propylamino)ethyl]-4-amino-5-chloro-2-methoxybenzamide was obtained.

Melting point: 108°–109° C. (recrystallized from isopropanol).

Elemental analysis for $C_{20}H_{25}N_3O_2Cl_2$:

|  | C% | H% | N% |
|---|---|---|---|
| Calculated: | 58.54 | 6.14 | 10.24 |
| Found: | 58.35 | 6.20 | 9.84 |

EXAMPLE 18

By following general method B using 1.22 g. of 3-ethylsulfonyl-6-methoxybenzoic acid and 1.14 g. of N-(p-chlorophenylmethyl)-N-n-propylethylenediamine, 1.8 g. of N-[2-(N'-p-chlorophenylmethyl-N'-n-propylamino)ethyl]-3-ethylsulfonyl-6-methoxybenzamide hydrochloride was obtained.

Melting point: 192°–193° C (recrystallized from methanol)

Elemental analysis for $C_{22}H_{30}N_2O_4S\ Cl_2$

|  | C% | H% | N% |
|---|---|---|---|
| Calculated: | 53.99 | 6.18 | 5.72 |
| Found: | 53.84 | 6.08 | 5.50 |

EXAMPLE 19

By following general method B using 1.0 g. of 4-amino-5-chloro-2-methoxybenzoic acid and 1.07 g. of N-ethyl-N-(p-methylthiophenylmethyl)ethylenediamine, 1.5 g. of N-[2-(N'-ethyl-N'-p-methylthiophenylmethylamino)ethyl]-4-amino-5-chloro-2-methoxybenzamide was obtained.

Melting point: 125°–126° C. (recrystallized from methanol).

Elemental analysis for $C_{20}H_{26}N_3O_2SCl$:

|  | C% | H% | N% |
|---|---|---|---|
| Calculated: | 58.88 | 6.42 | 10.30 |
| Found: | 59.40 | 6.79 | 10.31 |

EXAMPLE 20

By following general method B using 0.9 g. of 3-ethylsulfonyl-6-methoxybenzoic acid and 0.79 g. of N-(p-chlorophenylmethyl)-N-ethylethylenediamine, 1.4 g. of N-[2-(N'-p-chlorophenylmethyl-N'-ethylamino)ethyl]-3-ethylsulfonyl-6-methoxybenzamide hydrochloride was obtained.

Melting point: 165°–167° C. (recrystallized from methanol).

Elemental analysis for $C_{21}H_{28}N_2O_4SCl_2$:

|  | C% | H% | N% |
|---|---|---|---|
| Calculated: | 53.05 | 5.94 | 5.89 |
| Found: | 53.74 | 6.24 | 5.93 |

EXAMPLE 21

By following general method B using 1.14 g. of 4-amino-5-chloro-2-methoxybenzoic acid and 1.14 g. of N-(p-chlorophenylmethyl)-N-(isopropyl)ethylenediamine, 1.6 g. of N-[2-(N'-p-chlorophenylmethyl-N'-isopropylamino)ethyl]-4-amino-5-chloro-2-methoxybenzamide was obtained.

Melting point: 121° C. (recrystallized from isopropanol).

Elemental analysis for $C_{20}H_{25}N_3O_2Cl_2$:

|  | C% | H% | N% |
|---|---|---|---|
| Calculated: | 58.54 | 6.14 | 10.24 |
| Found: | 58.46 | 6.24 | 10.12 |

EXAMPLE 22

By following general method B using 0.9 g of 3-ethylsulfonyl-6-methoxybenzoic acid and 0.835 g. of N-(p-chlorophenylmethyl)-N-isopropylethylenediamine, 1.6 g. of N-[2-(N'-p-chlorophenylmethyl)-N'-isopropylamino)ethyl]-3-ethylsulfonyl-6-methoxybenzamide hydrochloride was obtained.

Melting point: 178°–179° C. (recrystallized from methanol).

Elemental analysis for $C_{22}H_{30}N_2O_4SCl_2$:

|  | C% | H% | N% |
|---|---|---|---|
| Calculated: | 53.99 | 6.18 | 5.72 |
| Found: | 53.23 | 6.38 | 5.39 |

EXAMPLE 23

By following general method B using 1.0 g. of 4-amino-5-chloro-2-methoxybenzoic acid and 1.2 g. of N-(p-chlorophenylmethyl)-N-n-butylethylenediamine, 1.8 g. of N-[2-(N'-n-butyl-N'-p-chlorophenylmethylamino)ethyl]-4-amino-5-chloro-2-methoxybenzamide was obtained.

Melting point: 115°–116° C. (recrystallized from methanol).

Elemental analysis for $C_{21}H_{27}N_3O_2Cl_2$:

|  | C% | H% | N% |
|---|---|---|---|
| Calculated: | 59.44 | 6.41 | 9.90 |
| Found: | 59.27 | 6.47 | 9.91 |

EXAMPLE 24

By following general method B using 1.0 g. of 4-amino-5-chloro-2-methoxybenzoic acid and 1.2 g. of N-(2',4'-dichlorophenylmethyl)-N-ethylethylenediamine, 1.6 g. of N-[2-(N'-2',4'-dichlorophenylmethyl)-N'-ethylamino)ethyl]-4-amino-5-chloro-2-methoxybenzamide was obtained.

Melting point: 95°–96° C. (recrystallized from a mixture of methanol and ether).

Elemental analysis for $C_{19}H_{22}N_3O_2Cl_3$:

|  | C% | H% | N% |
|---|---|---|---|
| Calculated: | 52.98 | 5.15 | 9.75 |
| Found: | 53.00 | 5.29 | 9.84 |

EXAMPLE 25

By following general method B using 0.9 g. of 3-ethylsulfonyl-6-methoxybenzoic acid and 0.9 g. of N-(2',4'-dichlorophenylmethyl)-N'-ethylethylenediamine, 1.5 g. of N-[2-(N'-2',4'-dichlorophenylmethyl)-N'-ethylamino)ethyl]-3-ethylsulfonyl-6-methoxybenzamide was obtained.

Melting point: 100°–101° C. (recrystallized from methanol).

Elemental analysis for $C_{21}H_{26}N_2O_4SCl_2$:

|  | C% | H% | N% |
|---|---|---|---|
| Calculated: | 53.28 | 5.54 | 5.92 |
| Found: | 53.30 | 5.61 | 5.96 |

EXAMPLE 26

By following general method B using 1.0 g. of 4-amino-5-chloro-2-methoxybenzoic acid and 0.93 g. of N-ethyl-N-(p-fluorophenylmethyl)-ethylenediamine, 1.5 g. of N-[2-(N'-ethyl-N'-p-fluorophenylmethylamino)ethyl]-4-amino-5-chloro-2-methoxybenzamide was obtained.

Melting point: 127°–128° C (recrystallized from methanol)

Elemental analysis for $C_{19}H_{23}N_3O_2ClF$:

|  | C% | H% | N% |
|---|---|---|---|
| Calculated: | 60.08 | 6.10 | 11.06 |
| Found: | 60.50 | 6.18 | 11.38 |

EXAMPLE 27

By following general method B using 1.2 g. of 3-ethylsulfonyl-6-methoxybenzoic acid and 1.1 g. of 2-(N-benzyl-N-methyl)amino-1-phenylethylamine, 1.0 g. of N-[2-(N'-benzyl-N'-methylamino)-1-phenylethyl]-3- ethylsulfonyl-6-methoxybenzamide was obtained. (purified by column chromatography).

Nuclear magnetic resonance spectra (CDCl₃):
δ(p. p. m.): 1.21 (3H, t), 2.30 (3H, s), 2.75 (2H, t), 3.10 (2H, q), 3.55 (2H, d), 4.00 (3H, s), 7.00–8.00 (14H, m)

EXAMPLE 28

By following general method B using 1 g. of 4-amino-5-chloro-2-methoxybenzoic acid and 1.3 g. of (N'-p-chlorophenylmethyl-N'-ethyl)-N-ethylethylenediamine, 2 g. of N-[2-(N'-p-chlorophenylmethyl-N'-ethylamino)ethyl]-N-ethyl-4-amino-5-chloro-2-methoxybenzamide hydrochloride was obtained.

Melting point: 144°–150° C. (recrystallized from a mixture of isopropanol and ether).

Elemental analysis for $C_{21}H_{28}N_3O_2Cl_3$:

|  | C% | H% | N% |
|---|---|---|---|
| Calculated: | 54.73 | 6.12 | 9.12 |
| Found: | 54.50 | 6.53 | 9.08 |

EXAMPLE 29

By following general method B using 1.0 g. of 4-amino-5-chloro-2-methoxybenzoic acid and 1.0 g. of N-p-chlorophenylmethyl-N-(β-diethylaminoethyl)ethylenediamine, 1.4 g. of N-[2-(N'-p-chlorophenylmethyl-N'-β-diethylaminoethyl)ethyl]-4-amino-5-chloro-2-methoxybenzamide was obtained.

Melting point: 94°–95° C. (recrystallized from a mixture of benzene and n-hexane).

Elemental analysis for $C_{23}H_{32}N_4O_2Cl_2$:

|  | C% | H% | N% |
|---|---|---|---|
| Calculated: | 59.10 | 6.90 | 11.99 |
| Found: | 58.85 | 7.30 | 11.93 |

EXAMPLE 30

By following general method C using 0.93 g. of 5-chloro-2-methoxybenzoic acid and 0.82 g. of N-benzyl-N-methylethylenediamine, 1.2 g. of N-[2-(N'-benzyl-N'-methylamino)ethyl]-5-chloro-2-methoxybenzamide hydrochloride was obtained.

Melting point: 158°–159° C. (recrystallized from isopropanol). Elemental analysis for $C_{18}H_{21}N_2O_2Cl.HCl$:

|  | C% | H% | N% |
|---|---|---|---|
| Calculated: | 58.54 | 6.00 | 7.59 |
| Found: | 58.22 | 5.97 | 7.60 |

EXAMPLE 31

By following general method C using 1.0 g. of 6-methoxy-3-methylthiobenzoic acid and 0.82 g. of N-benzyl-N-methylethylenediamine, 1.2 g. of N-[2-(N'-benzyl-N'-methylamino)ethyl]-6-methoxy-3-methylthiobenzamide hydrochloride was obtained.

Melting point: 124°–125° C. (recrystallized from isopropanol). Elemental analysis for $C_{19}H_{24}N_2O_2S.HCl$:

|  | C% | H% | N% |
|---|---|---|---|
| Calculated: | 59.91 | 6.61 | 7.35 |
| Found: | 59.55 | 6.77 | 7.07 |

EXAMPLE 32

By following general method C using 0.91 g. of 2,5-dimethoxybenzoic acid and 0.82 g. of N-benzyl-N-methylethylenediamine, 1.4 g. of N-[2-(N'-benzyl-N'-methylamino)ethyl]-2,5-dimethoxybenzamide hydrochloride was obtained.

Melting point: 130° C. (recrystallized from a mixture of isopropanol and ether).

Elemental analysis for $C_{19}H_{24}N_2O_3.HCl$:

|  | C% | H% | N% |
|---|---|---|---|
| Calculated: | 62.55 | 6.91 | 7.68 |
| Found: | 62.40 | 7.02 | 7.54 |

EXAMPLE 33

By following general method C using 0.91 g. of 2,5-dimethoxybenzoic acid and 1.07 g. of N-(p-chlorophenylmethyl)-N-ethylethylenediamine, 1.4 g. of N-[2-(N'-p-chlorophenylmethyl-N'-ethylamino)-ethyl]-2,5-dimethoxybenzamide fumarate was obtained.

Melting point: 102°–103° C. (recrystallized from a mixture of acetone and ether).

Elemental analysis for $C_{24}H_{29}N_2O_7Cl$:

|  | C% | H% | N% |
|---|---|---|---|
| Calculated: | 60.76 | 6.03 | 6.08 |
| Found: | 60.44 | 6.13 | 5.87 |

EXAMPLE 34

By following general method C using 1.08 g. of 5-chloro-2-methoxy-4-methylaminobenzoic acid and 0.82 g. of N-benzyl-N-methylethylenediamine, 1.15 g. of N-[2-(N'-benzyl-N'-methylamino)-ethyl]-5-chloro-2-methoxy-4-methylaminobenzamide hydrochloride was obtained.

Melting point: 213°–214° C.

Elemental analysis for $C_{19}H_{25}N_3O_2Cl_2$:

|  | C% | H% | N% |
|---|---|---|---|
| Calculated: | 57.29 | 6.33 | 10.55 |
| Found: | 57.30 | 6.37 | 10.27 |

Mass spectrum (m/e):
M⁺ 361, 363

EXAMPLE 35

By following general method D using 0.84 g. of 6-methoxy-3-sulfamoylbenzoic acid and 0.6 g. of N-benzyl-N-methylethylenediamine, 1.2 g. of N-[2-(N'-benzyl-N'-methylamino)ethyl]-6-methoxy-3-sulfamoylbenzamide was obtained.

Melting point: 202°–203° C. (recrystallized from a mixture of methanol and isopropanol).

Elemental analysis for $C_{18}H_{23}N_3O_4S$:

|  | C% | H% | N% |
|---|---|---|---|
| Calculated: | 57.28 | 6.14 | 11.13 |

-continued

|        | C%    | H%   | N%    |
|--------|-------|------|-------|
| Found: | 57.45 | 6.26 | 10.87 |

EXAMPLE 36

By following general method D using 0.94 g. of 6-methoxy-3-ethylaminosulfonylbenzoic acid and 0.6 g. of N-benzyl-N-methylethylenediamine, 0.94 g. of N-[2-(N'-benzyl-N'-methylamino)ethyl]-6-methoxy-3-ethylaminosulfonylbenzamide was obtained.

Melting point: 132°–133° C. (recrystallized from methanol).

Elemental analysis for $C_{20}H_{27}N_3O_4S$:

|             | C%    | H%   | N%    |
|-------------|-------|------|-------|
| Calculated: | 59.24 | 6.71 | 10.36 |
| Found:      | 58.98 | 6.77 | 10.21 |

EXAMPLE 37

By following general method B using 1.01 g. of 4-amino-5-chloro-2-methoxybenzoic acid and 1.0 g. of 2-aminomethyl-1-ethyl-5-phenylpyrrolidine, 1.8 g. of N-(1-ethyl-5-phenyl-2-pyrrolidinylmethyl)-4-amino-5-chloro-2-methoxybenzamide was obtained.

Melting point: 187°–188° C. (recrystallized from a mixture of methanol and isopropanol).

Elemental analysis for $C_{21}H_{26}N_3O_2Cl$:

|             | C%    | H%   | N%    |
|-------------|-------|------|-------|
| Calculated: | 65.02 | 6.76 | 10.83 |
| Found:      | 64.44 | 6.80 | 10.73 |

EXAMPLE 38

By following general method B using 1.01 g. of 4-amino-5-chloro-2-methoxybenzoic acid and 1.0 g. of 2-aminomethyl-1-benzyl-5-methylpyrrolidine, 1.5 g. of N-(1-benzyl-5-methyl-2-pyrrolidinylmethyl)-4-amino-5-chloro-2-methoxybenzamide was obtained.

Melting point: 136°–137° C. (recrystallized from isopropanol).

Elemental analysis for $C_{21}H_{26}N_3O_2Cl$:

|             | C%    | H%   | N%    |
|-------------|-------|------|-------|
| Calculated: | 65.02 | 6.76 | 10.83 |
| Found:      | 65.00 | 6.60 | 10.48 |

EXAMPLE 39

By following general method B using 1.01 g. of 4-amino-5-chloro-2-methoxybenzoic acid and 0.88 g. of 1-aminomethyl-2-ethylisoindoline, 1.3 g. of N-(1-ethyl-2-isoindolinylmethyl)-4-amino-5-chloro-2-methoxybenzamide was obtained.

Melting point: 185°–186° C. (decomp.) (recrystallized from isopropanol).

Elemental analysis for $C_{19}H_{22}N_3O_2Cl$:

|             | C%    | H%   | N%    |
|-------------|-------|------|-------|
| Calculated: | 63.42 | 6.16 | 11.68 |
| Found:      | 63.31 | 6.11 | 11.53 |

EXAMPLE 40

By following general method B using 0.9 g. of 5-ethylsulfonyl-2-methoxybenzoic acid and 0.76 g. of 2-aminomethyl-1-benzyl-5-methylpyrrolidine, 1.5 g. of N-(1-benzyl-5-methyl-2-pyrrolidinylmethyl)-5-ethylsulfonyl-2-methoxybenzamide hydrochloride was obtained.

Melting point: 172°–173° C. (recrystallized from ethanol).

Elemental analysis for $C_{23}H_{31}N_2O_4SCl$:

|             | C%    | H%   | N%   |
|-------------|-------|------|------|
| Calculated: | 59.15 | 6.69 | 6.00 |
| Found:      | 58.92 | 6.81 | 6.34 |

EXAMPLE 41

A mixture of 1 g. of 4-amino-5-chloro-2-methoxybenzoic acid 0.6 g. of triethylamine, and 10 ml. of methylene chloride was added dropwise 0.6 g. of ethyl chlorocarbonate at −10° – −15° C with stirring, the resultant mixture was maintained at the same temperature for 30 minutes. Then, 0.9 g. of N-benzyl-N-methylethylenediamine was added dropwise to the mixture at a temperature below 0° C. and the mixture was stirred for 3 hours at room temperature. The reaction mixture was acidified with 15 ml. of 1 normal hydrochloric acid and then an aqueous layer was separated from an organic layer formed. The organic layer was washed twice each with 20 ml. of water and the washings was combined with the aqueous layer recovered above and after alkalifying the mixture with 1 normal aqueous solution of sodium hydroxide, the reaction product was extracted thrice each with 20 ml. of methylene chloride. The extract recovered was dried over anhydrous potassium carbonate, the solvent was distilled off under reduced pressure, and the residue formed was recrystallized from a mixture of benzene and n-hexane to provide 1.1 g. of N-[2-(N'-benzyl-N'-methylamino)ethyl]-4-amino-5-chloro-2-methoxybenzamide.

Melting point: 119°–120° C.

Elemental analysis for $C_{18}H_{22}N_3O_2Cl$:

|             | C%    | H%   | N%    |
|-------------|-------|------|-------|
| Calculated: | 62.15 | 6.37 | 12.08 |
| Found:      | 61.78 | 6.52 | 11.95 |

EXAMPLE 42

A mixture of 0.9 g. of N-[2-(N'-ethyl-N'-p-methylthiophenylmethylamino)ethyl]-4-amino-5-chloro-2-methoxybenzamide and 1.5 ml. of 30% hydrogen peroxide solution was stirred in 10 ml. of acetic acid for one hour at room temperature.

After the reaction was over, the reaction mixture was alkalified with an aqueous sodium hydroxide solution and extracted twice each with 10 ml. of chloroform. The extracts were combined and dried over anhydrous magnesium sulfate. By distilling off chloroform, 0.9 g. of N-[2-(N'-ethyl-N'-p-methylsulfinylphenylmethylamino)ethyl]-4-amino-5-chloro-2-methoxybenzamide was obtained.

Nuclear magnetic resonance spectra (CDCl$_3$):

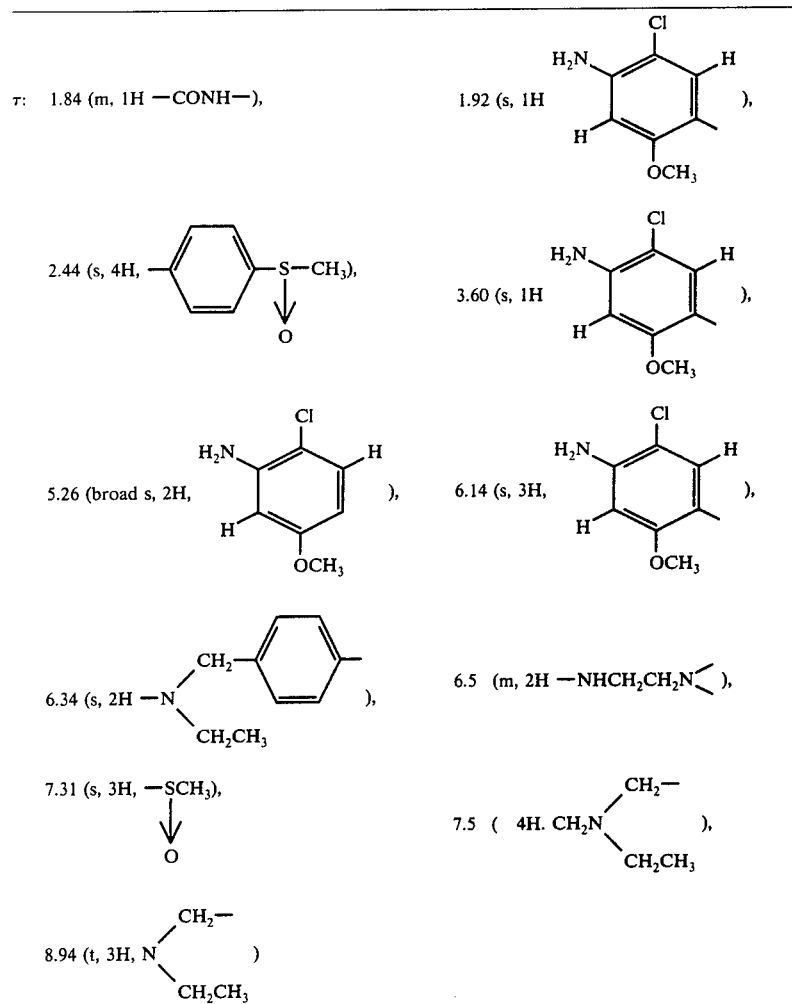

EXAMPLE 43

A mixture of 0.9 g. of N-[2-(N'-ethyl-N'-p-methylthiophenylmethylamino)ethyl]-4-amino-5-chloro-2-methoxybenzamide and 1.5 ml. of a 30% hydrogen peroxide — was stirred in 10 ml. of acetic acid for 24 hours at room temperature.

After reaction was over, the reaction mixture was treated as in Example 42 to provide 0.95 g. of N-[2-(N'-ethyl-N'-p-methylsulfonylphenylmethylamino)ethyl]-4-amino-5-chloro-2-methoxybenzamide.

Nuclear magnetic resonance spectra (CDCl₃):

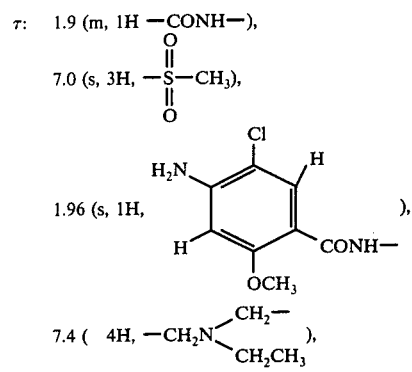

-continued

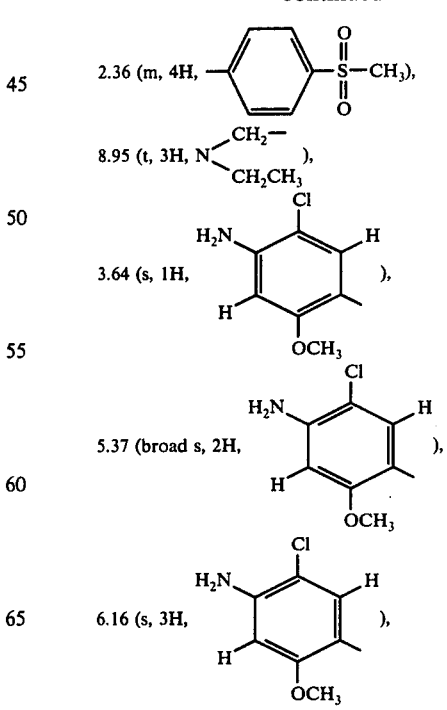

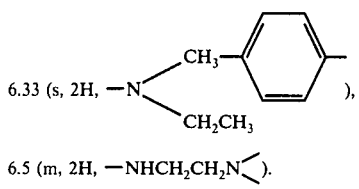

6.33 (s, 2H, —N(CH$_3$)(CH$_2$CH$_3$)—⟨phenyl⟩—), 6.5 (m, 2H, —NHCH$_2$CH$_2$N⟨ ).

Mass speactra (m/e): 439,441 (M$^+$)·

EXAMPLE 44

In 10 ml. of dichloromethane was suspended 1.0 g. of 4-amino-5-chloro-2-methoxybenzoic acid and then 0.84 ml. of triethylamine was added to the suspension to form a solution. After cooling the solution to a temperature of from −20° C. to −40° C., 0.53 ml. of ethyl chlorocarbonate was added dropwise to the solution followed by stirring for 0.5 hour. Then, 0.84 g. of N-ethyl-N-furfurylethylenediamine was added to the mixture at the same temperature as above followed by stirring for 0.5 hours and the mixture was further stirred for 2 hours at room temperature. After the reaction was over, the reaction mixture was washed twice each with 5 ml of 1 normal sodium hydroxide solution and then with water, dried over anhydrous magnesium sulfate, and the solvent was distilled off under reduced pressure to provide 1.7 g. of N-[2-(N'-ethyl-N'-furfurylamino)ethyl]-4-amino-5-chloro-2-methoxybenzamide.

Melting point: 109° C. (recrystallized from isopropanol)

Elemental analysis for $C_{17}H_{22}N_3O_3Cl$:

|  | C% | H% | N% |
|---|---|---|---|
| Calculated: | 58.04 | 6.30 | 11.94 |
| Found: | 57.75 | 6.20 | 11.90 |

EXAMPLE 45

In 20-30 ml. of dichloromethane was suspended 1.0 g. of 4-amino-5-chloro-2-methoxybenzoic acid and the 0.83 ml. of triethylamine was added to the suspension to form a solution. After cooling the solution to a temperature of from −10° to −20° C., 0.37 ml. of ethyl chlorocarbonate was added to the solution followed by stirring for 2 hours. Then, 0.99 g. of N-ethyl-N-(pyridin -2-yl)methylethylenediamine was added to the mixture at the same temperature and the resultant mixture was further stirred for 3 hours at room temperature. After the reaction was over, the reaction mixture was cooled and 20 ml. of 0.5 normal hydrochloric acid was added to the reaction mixture followed by shaking well. Thereafter, an aqueous layer formed was separated from the organic layer. The organic layer was further extracted twice each with 10 ml. of water and the aqueous extracts were combined with the aqueous layer. The mixture was washed with 10 ml. of dichloromethane, alkalified with a 1 normal aqueous solution of sodium hydroxide, and then the mixture was extracted thrice each with 10 ml. of dichloromethane. The extract was washed with water, dried, and the solvent was distilled off under reduced pressure. The residue was purified by a silica gel column chromatography using a mixture of chloroform and ethanol as an eluting solution to provide 0.85 g. of N-[2-{N'-ethyl-N'-(pyridin -2-yl)-methylamino}ethyl]-4-amino-5-chloro-2-methoxybenzamide.

Melting point: 100°-101° C.

Elemental analysis for $C_8H_{23}N_4O_2Cl$:

|  | C% | H% | N% |
|---|---|---|---|
| Calculated: | 59.58 | 6.39 | 15.44 |
| Found: | 59.02 | 6.44 | 15.02 |

EXAMPLE 46

A mixture of 1.50 g. of methyl 2-methoxy-4,5-azimidobenzoate and 1.54 g. of N-p-chlorophenylmethyl-N-ethylethylenediamine was refluxed in 7.5 ml. of toluene for 20 hours. The reaction mixture was cooled to room temperature and 10 ml. of 1 normal hydrochloric acid was added thereto followed by shaking.

The aqueous layer was separated and the pH value was adjusted to pH 8 with an aqueous sodium hydroxide solution, and the precipitates or an oily material formed was extracted twice each with 10 ml. of methylene chloride. The extracts were combined, dried over anhydrous magnesium sulfate, and the solvent was distilled off to provide 1.45 g of the crystals of N-{2-(N'-p-chlorophenylmethyl-N'-ethylamino)ethyl}-2-methoxy-4,5-azimidobenzamide.

Melting point: 129°-131° C. (recrystallized from a mixture of ethanol and water, needles)

Elemental analysis for $C_{19}H_{22}N_5O_2Cl$:

|  | C% | H% | N% |
|---|---|---|---|
| Calculated: | 58.84 | 5.72 | 18.06 |
| Found: | 59.33 | 5.77 | 17.98 |

EXAMPLE 47

In 20 ml. of dichloromethane was suspended 0.8 g. of 4-amino-5-chloro-2-methoxybenzoic acid and then 0.61 ml. of triethylamine was added to the suspension to form a solution. After cooling the solution to a temperature of from −20° C. to −25° C., 0.42 ml. of ethyl chlorocarbonate was added dropwise to the solution and the mixture was stirred for 30 minutes at the same temperature. Then, a solution of 0.7 g. of 4-amino-2-ethyl-1,2,3,4-tetrahydroisoquinoline in 5 ml. of dichloromethane was added dropwise to the mixture at the same temperature followed by stirring for 30 minutes and then the mixture was further stirred for 3 hours at room temperature. After the reaction was over, the reaction mixture was washed — with water, a diluted aqueous sodium hydroxide solution, and then water successively, and dried, and then the solvent was distilled off under reduced pressure. The oily material obtained crystallied shortly and the crystals thus formed were recrystallized from isopropanol to provide 1.25 g. of the white crystals of N-(2-ethyl-1,2,3,4-tetrahydro-4-isoquinolyl)-4-amino-5-chloro-2-methoxybenzamide.

Melting point: 181° C.

Elemental analysis for $C_{19}H_{22}N_3O_2Cl$:

|  | C% | H% | N% | Cl% |
|---|---|---|---|---|
| Calculated: | 63.42 | 6.16 | 11.68 | 9.85 |
| Found: | 63.33 | 6.17 | 11.84 | 10.17 |

EXAMPLE 48

In 20 ml. of dichloromethane was suspended 1.0 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added dropwise to the solution followed by stirring for 30 minutes at the same temperature. Then, a solution of 1.0 g. of 1-(2-aminoethyl)-2-phenylpyrrolidine in 5 ml. of dichloromethane was added dropwise to the solution at the same temperature followed by stirring for 30 minutes and then the mixture was further stirred for one hour at room temperature. The mixture was allowed to stand overnight. After the reaction was over, 20 ml. of a 10% aqueous solution of hydrochloric acid was added to the reaction mixture followed by shaking. Then, an aqueous layer formed was recovered, washed with a small amount of chloroform, and then alkalified with a 20% aqueous solution of sodium hydroxide to form crystals, which were recovered by filtration, washed with water, dried and recrystallized from isopropanol to provide 1.3 g. of N-[2-(2-phenylpyrrolidino)ethyl]-4-amino-5-chloro-2-methoxybenzamide.

Melting point: 170°-171° C.

Elemental analysis for $C_{20}H_{24}N_3O_2Cl$:

|  | C% | H% | N% | Cl% |
| --- | --- | --- | --- | --- |
| Calculated: | 64.25 | 6.47 | 11.24 | 9.48 |
| Found: | 63.98 | 6.49 | 11.10 | 9.98 |

EXAMPLE 49

In 20 ml. of dichloromethane was suspended 1.0 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added dropwise to the solution followed by stirring for 30 minutes at the same temperature. Thereafter, a solution of 0.8 g. of 2-(2-aminoethyl)-isoindoline in 5 ml. of dichloromethane was added dropwise to the solution at the same temperature as above followed by stirring for 30 minutes and then the mixture was allowed to stand over night at room temperature to form crystals. The crystals thus formed were recovered by filtration, washed with water, dried, and then recrystallized from dimethylformamide to provide 1.3 g. of N-[2-(2-isoindolinyl)ethyl]-4-amino-5-chloro-2-methoxybenzamide.

Melting point: 229°-230° C.

Elemental analysis for $C_{18}H_{20}N_3O_2Cl$:

|  | C% | H% | N% | Cl% |
| --- | --- | --- | --- | --- |
| Calculated: | 62.51 | 5.83 | 12.15 | 10.25 |
| Found: | 62.18 | 5.69 | 11.85 | 10.64 |

EXAMPLE 50

In 20 ml. of dichloromethane was suspended 1.0 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added dropwise to the solution with stirring followed by further stirring for 30 minutes at the same temperature. Then, a solution of 0.9 g. of 2-(2-aminoethyl)-1,2,3,4-tetrahydroisoquinoline in 5 ml. of dichloromethane was added dropwise to the solution at the same temperature as above followed by stirring for 30 minutes and then the mixture was further stirred for 3 hours at room temperature. After the reaction was over, 20 ml. of a 10% aqueous solution of hydrochloric acid was added to the reaction mixture and the mixture was shaked well. Thereafter, an aqueous layer formed was recovered, washed with a small amount of chloroform, and then alkalified with a 20% aqueous solution of sodium hydroxide to form a oily material, which crystallized soon. The crystals thus formed were recovered by filtration, washed with water, dried, and then recrystallized from dimethylformamide to provide 1.3 g. of the white crystals of N-[2-(1,2,3,4-tetrahydro-2-isoquinolyl)-ethyl]-4-amino-5-chloro-2-methoxybenzamide.

Melting point: 227° C.

Elemental analysis for $C_{19}H_{22}N_3O_2Cl$:

|  | C% | H% | N% | Cl% |
| --- | --- | --- | --- | --- |
| Calculated: | 63.42 | 6.16 | 11.68 | 9.85 |
| Found: | 63.28 | 6.16 | 11.71 | 10.09 |

EXAMPLE 51

In 20 ml. of dichloromethane was suspended 1.1 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added to the solution with stirring followed by further stirring for one hour at the same temperature. Thereafter, a solution of 0.97 g. of 1-benzyl-3-aminopyrrolidine in 5 ml. of dichloromethane was added dropwise to the mixture at the same temperature as above followed by stirring for 30 minutes at the same temperature and then the mixture was allowed to stand overnight at room temperature. After the reaction was over, the reaction mixture was washed — with water, a diluted aqueous sodium hydroxide solution, and then water, successively and dried, and then the solvent was distilled off under a reduced pressure. The residue formed was triturated with a small amount of ether to form crystals, which were recovered by filtration, washed with a small amount of ether and recrystallized from a mixture of benzene and n-hexane to provide 1.2 g. of the white crystals of N-(1-benzyl-3-pyrrolidinyl)-4-amino-5-chloro-2-methoxybenzamide.

Melting point: 116°-118° C.

Elemental analysis for $C_{19}H_{22}N_3O_2Cl$:

|  | C% | H% | N% | Cl% |
| --- | --- | --- | --- | --- |
| Calculated: | 63.42 | 6.16 | 11.68 | 9.85 |
| Found: | 63.24 | 5.92 | 11.48 | 10.13 |

EXAMPLE 52

In 30 ml. of dichloromethane was suspended 1.0 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added to the solution with stirring followed by further stirring for one hour at the same temperature. Then, a solution of 0.95 g. of 3-amino-1-benzyl-piperidine in 5 ml. of dichloromethane was added dropwise to the mixture at the same temperature as above followed by stirring for 30 minutes at the same temperature and then the mixture was further stirred for 30 minutes at room temperature. After the reaction was over, the reaction mixture was washed — with water, a diluted aqueous sodium hydroxide solution, and then water successively, and dried, and then the solvent was distilled off under a reduced pressure. To the oily residue formed was added a small amount of ether to form crystals, which were recovered by filtration and recrystallized from a mixture of acetone and n-hexane to provide 1.6 g. of N-(benzyl-3-piperidinyl)-4-amino-5-chloro-2-methoxybenzamide.

Melting point: 165° C.

Elemental analysis for $C_{20}H_{24}N_3O_2Cl$:

|  | C% | H% | N% | Cl% |
|---|---|---|---|---|
| Calculated: | 64.25 | 6.47 | 11.24 | 9.48 |
| Found: | 63.95 | 6.55 | 11.01 | 9.7813 |

EXAMPLE 53

In 30 ml. of dichloromethane was suspended 1.0 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added to the solution with stirring followed by further stirring for one hour at the same temperature. Then, a solution of 1.1 g. of 3-amino-1-p-chlorophenylmethylpyrrolidine in 5 ml. of dichloromethane was added dropwise to the mixture at the same temperature as above followed by stirring for 30 minutes at the same temperature and then the mixture was allowed to stand overnight at room temperature. After the reaction was over, the reaction mixture was extracted with a 10% aqueous hydrochloric acid and the extract was alkalified with a 40% aqueous solution of sodium hydroxide to form an oily material. The oily material thus formed was extracted with chloroform and the extract was washed with water and dried. The solvent was then distilled off from the residue under a reduced pressure and then a small amount of ether was added to the oily residue formed, whereby crystals were precipitated. The crystals were recovered by filtration and recrystallized from a mixture of benzene and n-hexane to provide 1.5 g. of N-(1-p-chlorophenylmethyl-3-pyrrolidinyl)-4-amino-5-chloro-2-methoxybenzamide.

Melting point: 109° C.

Elemental analysis for $C_{19}H_{21}N_3O_2Cl_2$:

|  | C% | H% | N% | Cl% |
|---|---|---|---|---|
| Calculated: | 57.88 | 5.37 | 10.66 | 17.98 |
| Found: | 57.66 | 5.24 | 10.60 | 18.0213 |

EXAMPLE 54

In 30 ml. of dichloromethane was suspended 1.0 g. of 4-amino-5-chloro-2-methoxybenzoic acid and then 0.75 ml. of triethylamine was added to the suspension to form a solution. After cooling the solution to a temperature of from −20° to −25° C., 0.55 ml. of ethyl chlorocarbonate was added to the solution with stirring followed by further stirring for one hour at the same temperature. Thereafter, a solution of 1.1 g. of 3-amino-1-p-methoxyphenylmethylpyrrolidine in 5 ml. of dichloromethane was added dropwise to the mixture at the same temperature as above followed by stirring further for 30 minutes at the same temperature and then the mixture was allowed to stand overnight at room temperature. After the reaction was over, the reaction mixture was washed, in succession, with water, a diluted aqueous—sodium hydroxide, and then water successively and dried, and then the solvent was distilled off under a reduced pressure. Then, 1.5 g. of the oily residue formed was dissolved in 5 ml. of methanol and after dissolving 0.5 g. of fumaric acid in the solution under heating, the solution was allowed to stand to form crystals, which were recovered by filtration and recrystallized from methanol to provide 1.4 g. of N-(1-p-methoxyphenylmethyl-3-pyrrolidinyl)-4-amino-5-chloro-2-methoxybenzamide fumarate.

Elemental analysis for $C_{20}H_{24}N_3O_3Cl \cdot C_4H_4O_4$:

|  | C% | H% | N% | Cl% |
|---|---|---|---|---|
| Calculated: | 56.97 | 5.58 | 8.31 | 7.01 |
| Found: | 56.76 | 5.51 | 8.56 | 6.6713 |

EXAMPLE 55

A mixture of 2.0 g. of 1-acetyl-5-chlorocarbonyl-6-methoxy-benzotriazole and 1.5 g. of 3-amino-N-benzyl-pyrrolidine was stirred in 15 ml. of methyl ethyl ketone for 2 days. After distilling off the solvent under a reduced pressure, a mixture of 2.63 ml. of concentrated hydrochloric acid and 15 ml. of ethanol were added to the residue formed followed by refluxing the mixture for 0.5 hour. Then, ethanol was distilled off under a reduced pressure and the residue formed was dissolved in 70 ml. of water. The aqueous solution was washed twice each with 50 ml. of chloroform and adjusted to pH about 7 with an aqueous sodium hydroxide solution to provide 1.2 g. of N-(1-benzyl-3-pyrrolidinyl)-2-methoxy-4,5-azimidobenzamide as precipitates.

Melting point: 149°–150° C. (recrystallized from ethanol, colorless prisms).

Elemental analysis for $C_{19}H_{21}N_5O_2$:

|  | C% | H% | N% |
|---|---|---|---|
| Calculated: | 64.94 | 6.02 | 19.93 |
| Found: | 64.86 | 6.02 | 19.91 |

EXAMPLE 56

By following the similar procedure as in Example 55 using 2.0 g. of 1-acetyl-5-chlorocarbonyl-6-methoxybenzotriazole and 1.65 g. of 3-amino-N-benzylpiperidine, 1.8 g. of N-(1-benzyl-3-piperidinyl)-2-methoxy-4,5-azimidobenzamide hydrochloride was obtained.

Melting point: 108°–109° C. (recrystallized from a mixture of ethanol and water, colorless needles).

Elemental analysis for $C_{20}H_{24}N_5O_2Cl$:

|  | C% | H% | N% |
|---|---|---|---|
| Calculated: | 59.77 | 6.02 | 17.43 |
| Found: | 60.09 | 5.75 | 17.32 |

EXAMPLE 57

By following general method A using 0.85 g. of 5-chloro-4-dimethylamino-2-methoxybenzoic acid and 0.65 g. of 3-amino-1-benzylpyrrolidine, 0.8 g. of N-(1-benzyl-3-pyrrolidinyl)-5-chloro-4-dimethylamino-2-methoxybenzamide was obtained.

Melting point: 85°–86° C

Elemental analysis for $C_{21}H_{26}N_3O_2Cl$:

|  | C% | H% | N% |
|---|---|---|---|
| Calculated: | 65.02 | 6.76 | 10.83 |
| Found: | 64.87 | 6.68 | 10.44 |

Mass spectrum (m/e): M+ 387, 389

EXAMPLE 58

By following general method C using 1.7 g. of 5-chloro-2-methoxy-4-methylaminobenzoic acid and 1.4 g. of 3-amino-1-benzylpyrrolidine, 2.1 g. of N-(1-benzyl-3-pyrrolidinyl)-5-chloro-2-methoxy-4-methylaminobenzamide hydrochloride was obtained.

Melting point: 124°–125° C

Elemental analysis for $C_{20}H_{25}N_3O_2Cl_2$:

|  | C% | H% | N% |
|---|---|---|---|
| Calculated: | 58.54 | 6.14 | 10.24 |
| Found: | 58.20 | 6.48 | 9.85 |

Mass spectrum (m/e): M+ 373,375

What is claimed is:

1. A benzamide compound represented by the formula:

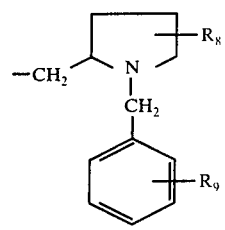

wherein X represents a lower alkoxy group; Y represents a hydrogen atom, an amino group, or a mono- or di-lower alkyl amino group; Z represents a halogen atom, a lower alkylthio group, a lower alkylsulfinyl group, a lower alkylsulfonyl group, a sulfamoyl group, or a lower alkylsulfamoyl group; and W represents a 1-ethyl-5-phenyl-2-pyrrolidinylmethyl group, a 2-(2-phenyl-pyrrolidino) ethyl group or a group shown by the formulae:

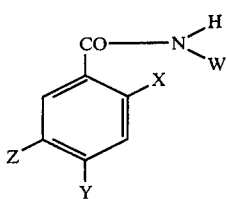 and

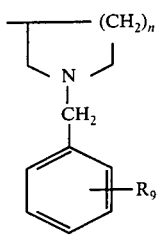

$R_8$ represents a lower alkyl group; $R_9$ represents a hydrogen atom, a halogen atom, or a lower alkoxy group; and n represents 1 or 2, and the pharmaceutically acceptable nontoxic salts thereof.

2. A benzamide compound as claimed in claim 1 represented by the formula

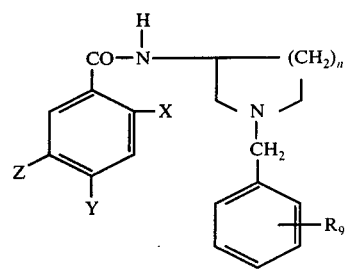

wherein X, Y, Z, $R_9$ and n have the same meanings as in claim 1 and the pharmaceutically acceptable nontoxic salts thereof.

3. A benzamide compound as claimed in claim 1 represented by the formula

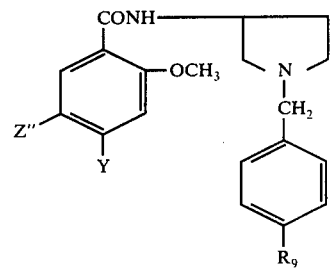

wherein Y represents a hydrogen atom, an amino group, a mono-, or di-lower alkyl amino group; Z" represents a halogen atom or an ethylsulfonyl group; and $R_9$ represents a hydrogen atom, a halogen atom, or a lower alkoxy group; and the pharmaceutically acceptable nontoxic salts thereof.

4. A benzamide compound according to claim 1, which is N-(1-Benzyl-3-pyrrolidinyl)-4-amino-5-chloro-2-methoxybenzamide.

5. A benzamide compound as claimed in claim 1 represented by the formula

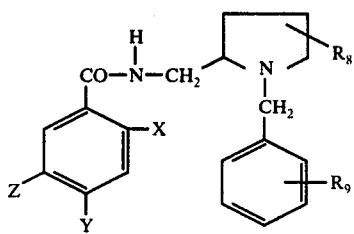

wherein X, Y, Z, $R_8$ and $R_9$ have the same meanings as in claim 1 and the pharmaceutically acceptable nontoxic salts thereof.

6. A benzamide compound as claimed in claim 1 represented by the formula

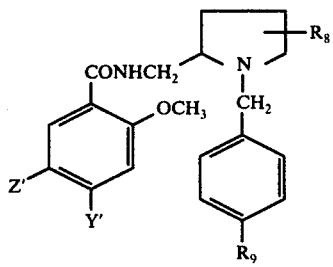

wherein Y' represents a hydrogen atom, an amino group, a mono- or di-lower alkylamino group, Z' represents a halogen atom or an ethylsulfonyl group, and $R_8$ and $R_9$ have the same meanings as in claim 1 and the pharmaceutically acceptable nontoxic salt thereof.

7. A benzamide compound according to claim 1 which is N-(1-Benzyl-5-methyl-2-pyrrolidinylmethyl)-4-amino-5-chloro-2-methoxybenzamide.

8. A benzamide compound according to claim 1 which is N-(1-Benzyl-5-methyl-2-pyrrolidinylmethyl)-5-ethylsulfonyl-2-methoxybenzamide.

9. A benzamide compound as claimed in claim 1 represented by the formula

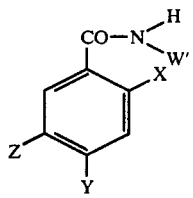

wherein W' represents a 1-ethyl-5-phenyl-2-pyrrolidinylmethyl group, a 2-(2-phenylpyrrolidino)ethyl group, and X, Y, and Z have the same meanings as in claim 1 and the pharmaceutically acceptable nontoxic salt thereof.

10. A benzamide compound as claimed in claim 9 represented by the formula

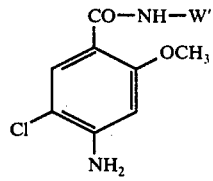

wherein W' has the same meaning as in claim 9 and the pharmaceutically acceptable nontoxic salt thereof.

11. N-(1-Benzyl-3-pyrrolidinyl)-5-chloro-4-dimethylamino-2-methoxybenzamide.

12. N-(1-Benzyl-3-pyrrolidinyl)-5-chloro-2-methoxy-4-methylaminobenzamide and the pharmaceutically acceptable nontoxic salts thereof.

13. N-(1-p-chlorophenylmethyl-3-pyrrolidinyl)-4-amino-5-chloro-2-methoxybenzamide.

* * * * *